United States Patent [19]

Rosenfeld et al.

[11] 4,376,226
[45] Mar. 8, 1983

[54] PROCESS FOR THE SEPARATION OF ORTHO AROMATIC ISOMERS BY SELECTIVE ADSORPTION

[75] Inventors: Daniel D. Rosenfeld, Houston, Tex.; David E. W. Vaughan, Flemington, N.J.

[73] Assignee: Exxon Research & Engineering Co., Florham Park, N.J.

[21] Appl. No.: 346,150

[22] Filed: Feb. 5, 1982

[51] Int. Cl.³ .............................................. C07C 7/12
[52] U.S. Cl. ..................................... 585/828; 585/826
[58] Field of Search ......................... 585/826, 827, 828

[56] References Cited

U.S. PATENT DOCUMENTS

| | | | |
|---|---|---|---|
| 3,558,730 | 1/1971 | Neuzil | 260/674 |
| 3,558,732 | 1/1971 | Neuzil | 260/674 |
| 3,626,020 | 12/1971 | Neuzil | 260/674 |
| 3,636,121 | 1/1972 | Stine et al. | 585/828 |
| 3,663,638 | 5/1972 | Neuzil | 260/674 |
| 3,939,221 | 2/1976 | Pearce | 585/828 |
| 3,943,182 | 3/1976 | Neuzil et al. | 260/674 |
| 3,997,619 | 12/1976 | Neuzil | 260/674 |
| 3,998,901 | 12/1976 | Neuzil et al. | 260/674 |
| 4,021,499 | 5/1977 | Bieser | 260/674 |
| 4,309,313 | 1/1982 | Barrett et al. | 252/455 Z |

FOREIGN PATENT DOCUMENTS 1354716  5/1974  United Kingdom ............... 585/828

Primary Examiner—Delbert E. Gantz
Assistant Examiner—A. Pal
Attorney, Agent, or Firm—Mitchell D. Bittman

[57] ABSTRACT

An improved process for separating ortho aromatic isomers from a feed stream containing a mixture of aromatics by contacting the feed stream with a bed of the crystalline aluminosilicate adsorbent CSZ-1. The adsorbed ortho aromatic isomer is removed from the adsorbent by desorption.

18 Claims, No Drawings

PROCESS FOR THE SEPARATION OF ORTHO AROMATIC ISOMERS BY SELECTIVE ADSORPTION

BACKGROUND OF THE INVENTION

The field of art to which the claimed invention pertains is hydrocarbon separation. More specifically, the claimed invention relates to the separation of ortho aromatic isomers from a hydrocarbon feed stream containing a mixture of aromatics by use of a specific crystalline aluminosilicate adsorbent which selectively removes the ortho aromatic isomer from the feed stream. The selectively adsorbed ortho aromatic isomer is removed from the adsorbent through a desorption step.

DESCRIPTION OF THE PRIOR ART

It is known in the separation art that certain adsorbents generally comprising crystalline aluminosilicates can be utilized to separate certain hydrocarbons from mixtures thereof. In aromatic hydrocarbon separation and in particular the separation of $C_8$ aromatic isomers, it is generally recognized that certain crystalline aluminosilicates containing selected cations at the zeolitic cationic sites enhances selectivity of the zeolite for a given $C_8$ aromatic isomer. This manner of separation is particularly useful when the components to be separated have similar physical properties, such as freezing and boiling points.

A number of processes describing the separation of para-xylene from a mixture of at least one other xylene isomer utilizing a crystalline aluminosilicate adsorbent, are shown in U.S. Pat. Nos. 3,558,730, 3,558,732, 3,626,020, and 3,663,638. Other processes which describe the adsorption separation of ethylbenzene from a mixture of xylene isomers utilizing a crystalline aluminosilicate adsorbent are shown in U.S. Pat. Nos. 3,943,182, 3,997,619, 3,998,901, and 4,021,499. However, while the separation of paraxylene and ethylbenzene from a feed stream mixture is known in the art, the separation of ortho-xylene or other ortho aromatic isomers from a feed stream mixture is not common in the art.

Ortho aromatic isomers, such as ortho-xylene, are used commercially as precursers from phthalate plasterizers, but the availability of the ortho aromatic isomers is restricted due to the inability to effectively separate the ortho aromatic isomers from a mixture of aromatics, such as a mixture of $C_8$ aromatics which include at least one of para-xylene, meta-xylene, and ethylbenzene in addition to ortho-xylene.

SUMMARY OF THE INVENTION

It is accordingly a broad objective of our invention to provide a process of separation of ortho aromatic isomers from a hydrocarbon feed stream containing a mixture of aromatics.

In brief, the invention comprises an adsorptive separation process for the separation of the ortho aromatic isomers from a hydrocarbon feed stream containing a mixture of aromatics by contacting the hydrocarbon feed stream with a bed of the crystalline aluminosilicate adsorbent CSZ-1. A raffinate stream is then withdrawn from the bed, this stream containing less of the selectively adsorbed ortho aromatic isomer. The adsorbed ortho aromatic isomer on the bed is then desorbed to effect displacement of the ortho aromatic isomer, followed by withdrawing from the adsorbent bed an extract stream containing the ortho aromatic isomer. The preferred hydrocarbon feed stream is a mixture of $C_8$ aromatics, while the preferred CSZ-1 adsorbent is cation exchanged to increase the ortho aromatic selectivity of the adsorbent.

DETAILED DESCRIPTION OF THE INVENTION

Hydrocarbon feed streams which can be utilized in the process of this invention contain mixtures of aromatics and ortho aromatic isomer. This generally involves a $C_8$, $C_9$, or $C_{10}$ aromatic feed stream, with the preferred feed stream being $C_8$ aromatics containing ortho-xylene and at least one of para-xylene, meta-xylene, and ethylbenzene. Ortho aromatic isomers are defined as aromatics rings which contain at least one substituent group adjacent to another substituent group in the ring, i.e., having at least one group which has an ortho position relative to one other group of the aromatic ring. For $C_8$ aromatics it is ortho-xylene, while in the case of the $C_9$ aromatic, trimethylbenzene, it is pseudocumene and hemimelletene. Mixtures containing substantial quantities of ortho aromatic isomers and other aromatics generally are produced by reforming and isomerization processes, processes which are well known to the refining and petrochemical arts.

The hydrocarbon feed stream is then contacted with a bed of a crystalline aluminosilicate adsorbent, entitled CSZ-1, having a composition in terms of mole ratios of oxides of 0.05 to 0.55 cesium and/or thallium (Cs, Tl)$_2$O:0.45 to 0.95 Na$_2$O:Al$_2$O$_3$:3 to 7 SiO$_2$:X H$_2$O where X is 0 to 10. The sodium ion content can be reduced as a result of cation exchanging. The use of this specific crystalline aluminosilicate adsorbent, CSZ-1, is critical to the selective adsorption of ortho aromatic isomers, preferably ortho-xylene. This specific crystalline aluminosilicate adsorbent, CSZ-1, is fully identified and described in U.S. Pat. No. 4,309,313 by Barrett and Vaughan, issued Jan. 5, 1982, this disclosure being fully incorporated herein by reference. While the adsorbent is fully described in this patent, it has been surprisingly found that this adsorbent is ortho selective in a feedstream containing a mixture of aromatics, particularly aromatic isomers. Further, the ortho selectivity can be substantially increased by cation exchanging the adsorbent with a suitable cation.

In order to substantially increase the selectivity of the adsorbent for ortho aromatic isomers, the adsorbent which is available in its sodium-cesium form is preferably cation exchanged. The sodium can be exchanged with suitable cations which include base metal or transition metal cations, such as copper, rubidium, nickel, strontium, cobalt, potassium, lead, barium, lithium, cadmium, cesium and calcium, or mixtures thereof or other cations, such as ammonium and hydrogen. The preferred cations for increased selectivity are potassium, lead, barium, lithium, ammonium and cadmium, with the preferred combination of cations being potassium with either barium or lead.

The CSZ-1 adsorbent can be combined with a binder, such as natural or synthetic clays (e.g. Koalin), inorganic oxides, and lubricants (e.g. graphite) and can be in any form acceptable to the separation process such as extrudates, spheres, granules or tablets.

Certain characteristics of adsorbents are highly desirable, if not absolutely necessary, to the successful operation of a selective adsorption process. Among such characteristics are: adsorptive capacity from some weight of the ortho aromatic isomer per weight of adsorbent; and the selective adsorption of the ortho aromatic isomer with respect to a raffinate component and the desorbent material.

Capacity of the adsorbent for adsorbing a specific volume of ortho aromatic isomer is, of course, a necessity; without such capacity the adsorbent is useless for adsorptive separation. Furthermore, the higher the adsorbent's capacity for the ortho aromatic isomer, the better is the adsorbent. Increased capacity of a particular adsorbent makes it possible to reduce the amount of adsorbent needed to separate the ortho aromatic isomer contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. Generally, the adsorbent of this invention has a capacity of at least 5% of hydrocarbon by weight of adsorbent and preferably at least 8% of hydrocarbon by weight of adsorbent.

The second necessary adsorbent characteristic is the ability of the adsorbent to separate components of the feed; or, in other words, that the adsorbent possess adsorptive selectivity, ($\alpha$), for one component as compared to another component. Relative selectivity can be expressed not only for one feed component as compared to another but can also be expressed between any feed mixture component and the desorbent material. The separation factor, ($\alpha$), as used throughout this specification is defined as the ratio of the two components of the adsorbed phase over the ratio of the same two components in the unadsorbed phase at equilibrium conditions.

Realtive selectivity is shown as Equation 1 below:

$$\text{Selectivity} = (\alpha) = \frac{[\text{weight } C/\text{weight } D]_A}{[\text{weight } C/\text{weight } D]_U} \quad \text{EQUATION 1}$$

where C and D are two components of the feed represented by weight and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occuring between the unadsorbed and adsorbed phases.

Where selectivity of two components approaches 1.0 there is no preferential adsorption of one component by the adsorbent with respect to the other; they are both adsorbed (or nonadsorbed) to about the same degree with respect to each other. As the ($\alpha$) becomes less than or greater than 1.0 there is preferential adsorption by the adsorbent for one component with respect to the other. When comparing the selectivity by the adsorbent of one component C over component D, at ($\alpha$) larger than 1.0 indicates preferential adsorption of component C within the adsorbent. An ($\alpha$) less than 1.0 would indicate that component D is preferentially adsorbed leaving an unadsorbed phase richer in component C and an adsorbed phase richer in component D. For optimum performance desorbent materials should have a selectivity equal to about 1 or less than 1 with respect to all extract components so that all of the extract components can be extracted as a class and all raffinate components clearly rejected into the raffinate stream. When the adsorbent of this invention is cation exchanged it is preferably exchanged with a cation which will impart an ($\alpha$) separation factor of at least 2.0 of the ortho aromatic isomer (component C) over at least one of the other components (component D) of the hydrocarbon feed stream.

In order to test the various cation exchanged CSZ-1 adsorbent materials with a particular feed mixture to measure the characteristics of adsorptive capacity and selectivity, a static testing procedure was employed. The procedure consisted of contacting a known weight of adsorbent with a known weight of mixed hydrocarbon feed stream. After allowing this mixture to reach equilibrium, a sample was removed and analyzed by gas chromatography. The amount of isomers in the raffinate were measured and the amount of isomers adsorbed were obtained by difference from the standard feed stream.

In a separation process, after the hydrocarbon feed stream is contacted with the bed of adsorbent, a raffinate stream is withdrawn from the adsorbent bed, this stream containing less of the selectively adsorbed ortho aromatic isomer of the feed stream. Then the adsorbed aromatic isomer on the bed is desorbed to effect displacement thereof.

The desorbing step which can be used in the various processing schemes employing this adsorbent will vary depending on the type of operation employed. The term "desorbent material" as used herein shall mean any fluid substance capable of removing a selectively adsorbed ortho aromatic isomer from the adsorbent. In the swing-bed system in which the selectively adsorbed ortho aromatic isomer is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed ortho aromatic isomer from the adsorbent.

However, in an adsorptive separation process which employs the adsorbent and which is generally operated at substantially constant pressures and temperatures to insure a liquid phase, the desorbent material relied upon must be judiciously selected to satisfy several criteria. First, the desorbent material must displace the ortho aromatic isomer from the adsorbent with reasonable mass flow rates without itself being so strongly adsorbed as to unduly prevent the ortho aromatic isomer from displacing the desorbent material in a following adsorption cycle. Expressed in terms of the selectivity, it is preferred that the adsorbent be more selective for the ortho aromatic isomers with respect to a raffinate (e.g. other isomers), than it is for the desorbent material with respect to a raffinate. Secondly, desorbent materials must be compatible with the particular adsorbent and the particular feed stream. More specifically they must not reduce or destroy the critical selectivity of the adsorbent for the ortho aromatic isomers with respect to the raffinate.

Desorbent materials to be used in the process of this invention should additionally be substances which are easily separable from the feed stream that is passed into the process. After desorbing the ortho aromatic isomer of the feed, both desorbent material and the ortho aromatic isomers are removed in a mixture from the adsorbent. Without a method of separating the desorbent material, such as distillation, the purity of either the ortho aromatic isomer or the raffinate component would not be very high. It is therefore contemplated that any desorbent material used in this process will have a substantially different average boiling point than that of the feed stream. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture.

In a liquid-phase operation of the process of our invention, desorbent materials comprising mono-aromatic hydrocarbons are effective. Mixtures of toluene with paraffins are also effective as desorbent materials. Such paraffins must be compatible with the adsorbent and feed stream as described above and must be easily separable from the feed stream. The paraffins can include straight or branched chain paraffins or cycoparaffins which meet these criteria. Typical concentrations of toluene in such mixtures can be from a few volume percent up to 100 volume % of the total desorbent material mixture but such concentrations preferably will be within the range of from about 50 volume % to about 100 volume % of the mixture. Other desorbents include benzene, diethylbenzene, etc. and mixtures thereof.

Following desorption, the extract stream containing the ortho aromatic isomer is withdrawn from the adsorbent bed. Depending on the separation factor ($\alpha$) this withdrawn extract can contain relatively pure fractions or ortho aromatic isomer. However, it will be appreciated that the selecitvely adsorbed component is never completely adsorbed by the adsorbent, nor is the raffinate component completely non-adsorbed by the adsorbent.

In general, this adsorptive-separation process can be carried in the vapor or liquid phase, while the liquid phase is preferable. Adsorption conditions for the process of this invention may include temperatures within the range of from about ambient to about 450° F. (235° C.) and will include pressures in the range from about atmospheric to about 500 psig. Desorption conditions for the process of the invention shall generally include the same range of temperatures and pressures as described for the adsorption operation. The desorption of the selectively adsorbed ortho aromatic isomer could also be effected at subatmospheric pressures or elevated temperatures or both, or by vacuum purging of the adsorbent to remove the adsorbed isomer, but this process is not primarily directed to these desorption methods.

EXAMPLE I

A crystalline aluminosilicate adsorbent of CSZ-1 having a Si/Al atom ratio of 2.8, and a Cs/Al atom ratio of 0.35 in its sodium form was cation exchanged with the cations and to the extent listed in Table 1. A $C_8$ aromatic feed stream containing 1% of ethylbenzene, 1% of para-xylene, 1% of ortho-xylene, 2% of meta-xylene, 2% of n-nonane and 93% of n-hexane, all by weight, was added at ambient temperature to the various cation exchanged CSZ-1 adsorbents, as listed in Table 1. After allowing this mixture to reach equilibrium, the mixture was allowed to settle and a sample was removed and analyzed by gas chromatography. The amount of $C_8$ isomers in the raffinate were measured and the amount of isomers adsorbed were obtained by difference from the standard feed stream. The capacity and the ($\alpha$) separation factor were calculated for ortho-xylene (OX) versus each of meta-xylene (MX), ethylbenzene (EB), and para-xylene (PX), as listed in the following Table 1:

TABLE 1

| Cation | CAPACITY GMS C8 ADSORBED GM ADSORBENT | "α" SEPARATION FACTOR | | | % Na EXCHANGED |
|---|---|---|---|---|---|
| | | OX/MX | OX/EB | OX/PX | |
| Na | .088 | 1.4 | 1.9 | 1.8 | |
| K | .091 | 2.5 | 1.4 | 1.3 | 93 |
| Cs | .075 | 1.5 | 1.0 | 1.6 | |
| Pb | .067 | 3.0 | 2.5 | 2.2 | 97 |
| Ba | .088 | 2.2 | 2.2 | 1.3 | 92 |
| Li | .092 | 1.5 | 2.2 | 2.1 | 71 |
| Cu | .040 | 1.5 | 1.8 | 1.5 | 90 |
| Co | .064 | 1.6 | 1.7 | 1.5 | 85 |
| Rb | .080 | 2.0 | 1.1 | 1.7 | |
| Sr | .075 | 2.0 | 1.7 | 1.7 | |
| Fe | .048 | 1.4 | 1.5 | 1.3 | 86 |
| Ca | .067 | 1.7 | 1.6 | 1.6 | 90 |
| Cd | .020 | 2.2 | 2.1 | 2.0 | 89 |
| Zn | .021 | 1.5 | 1.6 | 1.4 | 84 |
| Ni | .089 | 2.0 | 1.7 | 1.6 | 69 |
| NH4 | .016 | 1.6 | 3.7 | 2.4 | 87 |
| K/Ba | .086 | 2.7 | 2.3 | 1.7 | |
| K/Pb | .016 | 3.5 | 2.3 | 2.2 | |

As can be seen from Table 1, exchanged forms containing the cations lead, cadmium, ammonium and mixtures of potassium with either barium or lead showed particularly good selectivity.

EXAMPLE II

A crystalline aluminosilicate adsorbent of CSZ-1 having a Si/Al atom ratio of 2.8 and a Cs/Al atom ratio of 0.35 in its sodium form was cation exchanged with the cations and to the extend listed in Table 2. A standard $C_9$ aromatic feed stream containing 1.9% of pseudocumene, 1.9% of mesitylene, 1.9% of hemimelletene, 1.9% of n-nonane in a solution of n-hexane, all percents being by weight, was added at ambient temperature to the various cation exchanged CSZ-1 adsorbents, as listed in Table 2. After allowing the mixture to reach equilibrium, a sample was removed and analyzed by gas chromatography. The amount of $C_9$ isomers in the raffinate were measured and the amount of isomers adsorbed were measured by the difference with the standard feed stream. The capacity and the ($\alpha$) separation factor were calculated for the various components of the feedstream, as listed in the following Table 2:

TABLE 2

| | "α" Separation Factor | | | |
|---|---|---|---|---|
| Cation | Pseudo-cumene Mesitylene | Pseudo-cumene Hemi-melletene | Hemi-melletene Mesitylene | Capacity gms $C_9$ adsorbed gm adsorbent |
| K+ | 2.4 | 0.9 | 2.6 | 0.12 |
| Pb+2 | 4.2 | 0.8 | 5.2 | 0.08 |
| Ca+2 | 2.1 | 0.6 | 3.5 | 0.10 |
| Li+ | 1.3 | 0.7 | 2.0 | 0.18 |
| Ba+2 | 2.9 | 0.8 | 3.8 | 0.09 |
| NH4+ | 2.5 | 0.8 | 3.2 | 0.08 |
| Co+2 | 2.1 | 0.8 | 2.5 | 0.09 |
| Sr+2 | 2.4 | 0.6 | 3.8 | 0.10 |
| Cs+ | 2.0 | 1.4 | 2.1 | 0.09 |

As can be seen from Table 2, exchanged forms of CSZ-1 containing the cations lead, barium and strontium showed particularly good selectivity for both pseudocumene and hemimelletene over mesitylene.

EXAMPLE III

A $C_9$ aromatic feed stream containing 2.1% of para ethyl toluene (P), 1.7% of meta ethyl toluene (M), 1.7% of ortho ethyl toluene (D), 1.9% of n-nonane in a solution of n-hexane, all percents being by weight, was added to a CSZ-1 cation exchanged as in Example II. The capacity and the ($\alpha$) separation factor were calculated for the various components of the feed stream, as listed in the following Table 3:

TABLE 3

| | "α" Separation Factor | | | |
|---|---|---|---|---|
| Cation | $\frac{O}{P}$ | $\frac{O}{M}$ | $\frac{P}{M}$ | Capacity gms $C_9$ adsorbed gms adsorbent |
| K+ | 1.4 | 2.4 | 1.7 | 0.12 |
| Pb+2 | 2.1 | 2.8 | 1.4 | 0.08 |

As can be seen from Table 3 the lead cation exchanged form of CSZ-1 showed particularly good selectiity for ortho ethyl toluene over both para ethyl toluene and meta ethyl toluene.

EXAMPLE IV

A separation process was carried out utilizing as an adsorbent CSZ-1 having a Si/Al atom ratio of 2.8, a Cs/Al atom ratio of 0.35 in its sodium form, and having been cation exchanged with potassium.

Two three foot sections of liquid chromatography tubing were connected in series with a dead volume connector after being packed with powdered potassium exchanged CSZ-1. The column was then flushed with a desorbent mixture of toluene and paraffin "F", before 200 ul of a 50/50 (volume) ortho-xylene/meta-xylene mixture was injected. The flow rates of desorbent was 0.15 ml per minute with a back pressure of 600 psi. Samples were taken every three minutes and analyzed for xylene isomers via gas chromatography. The separation process was carried out at at ambient temperature.

The calculated "$\alpha$" separation factor was 2.0 with a resolution of 0.72 (a resolution of 1.0 would indicate baseline or complete separation of components).

What is claimed is:
1. An adsorptive separation process for separating the ortho aromatic isomers from a hydrocarbon feed stream containing a mixture of aromatics comprising:
   (a) contacting said hydrocarbon feed stream with a bed of a crystalline aluminosilicate adsorbent of CSZ-1;
   (b) withdrawing from said bed of adsorbent a raffinate stream containing less of the selectively adsorbed ortho aromatic isomer of the feed stream;
   (c) desorbing the adsorbed ortho aromatic isomer to effect displacement thereof; and
   (d) withdrawing from the adsorbent bed an extract stream containing the ortho aromatic isomer.
2. Process of claim 1 further characterized in that said adsorbent contains at least one cation selected from the group consisting of potassium, lead, barium, lithium, cadmium, ammonium, sodium, copper, rubidium, nickel, strontium, cobalt, cesium and calcium.
3. Process of claim 2 wherein the adsorbent has at least one cation chosen from the group consisting of potassium, lead, barium, lithium, ammonium and cadmium.
4. Process of claim 3 wherein the adsorbent has a cation of potassium combined with a cation chosen from the group consisting of barium and lead.
5. Process of claim 2 wherein the adsorbed aromatic components are desorbed by passing a desorbent material through said bed.
6. Process of claims 2, 3, 4, or 5 wherein the hydrocarbon feed stream contains a mixture of ortho-xylene and at least one of the aromatics selected from the group consisting of para-xylene, meta-xylene and ethylbenzene.
7. Process of claims 1, 2, 3, 4, or 5 wherein the hydrocarbon feed stream contains a mixture of $C_9$ aromatics.
8. Process of claims 1, 2 3, 4 or 5 wherein the hydrocarbon feed stream contains a mixture of $C_{10}$ aromatics.
9. Process of claims 1 or 2 further characterized in that said adsorbent contains at least one cation which imparts an ($\alpha$) separation factor of at least 2.0 of the ortho aromatic isomer over at least one of the other components of the hydrocarbon feed stream.
10. Process of claim 5 wherein the desorbent is selected from the group consisting of toluene, benzene, paraffin, diethylbenzene and mixtures thereof.
11. Process of claim 1 wherein the adsorbent has a formula in terms of mole ratios of oxides of $0.05-0.55 M_2O:0.45$ to $0.95 Na_2O:Al_2O_3:3-7SiO_2:XH_2O$ where M is cesium or thallium and X is 0 to 10.
12. Process of claim 11 wherein the adsorbent has a reduced sodium ion content as a result of having been cation exchanged.
13. Process of claim 1 wherein the separation is carried out at a temperature within the range of ambient to 450° F. and a pressure within the rante of atmospheric to 500 psig.
14. Process of claim 13 wherein the process is caried out in the liquid phase.
15. Process of claim 1 wherein the process is carried out in the vapor phase.
16. Process of claim 1 wherein the adsorbent is combined with a binder.
17. Process of claim 16 wherein the binder is selected from the group consisting of natural and synthetic clays, inorganic oxides, and lubricants.
18. Process of claim 9 further characterized in that said adsorbent has a capacity of at least 5% of hydrocarbon by weight of adsorbent.

* * * * *